United States Patent [19]
Meltzer

[11] Patent Number: 5,647,379
[45] Date of Patent: Jul. 15, 1997

[54] CORRELATOR BASED ELECTROMAGNETIC INTERFERENCE RESPONSIVE CONTROL SYSTEM USEFUL IN MEDICAL DEVICES

[75] Inventor: Mark J. Meltzer, San Francisco, Calif.

[73] Assignee: Ventritex, Inc., Sunnyvale, Calif.

[21] Appl. No.: 343,294

[22] Filed: Nov. 22, 1994

[51] Int. Cl.⁶ ................................................. A61N 1/00
[52] U.S. Cl. ................................................................ 128/897
[58] Field of Search ................................. 128/696–702, 128/899, 897, 901, 903; 607/4–9, 32; 324/613; 343/703

[56] References Cited

U.S. PATENT DOCUMENTS

| | | |
|---|---|---|
| 3,688,776 | 9/1972 | Kenny . |
| 3,985,142 | 10/1976 | Wickham . |
| 4,091,818 | 5/1978 | Brownleee et al. . |
| 4,516,579 | 5/1985 | Irnich . |
| 4,913,146 | 4/1990 | DeCote, Jr. . |
| 5,178,140 | 1/1993 | Ibrahim . |
| 5,197,468 | 3/1993 | Proctor et al. . |
| 5,246,000 | 9/1993 | Ellis et al. .............................. 607/27 |

OTHER PUBLICATIONS

"Technical Tricks All About Correlators" R.H. Roberts, Feb. 1993. pp. 10–11.
"Interference in Pacemakers" Werner Irnich, PACE, vol. 7, Nov.–Dec. 1984, Part I, pp. 1021–1048.
"Performance Degradation of Electronic Medical Devices Due to Electromagnetic Interference", Jeffrey L. Silberberg, Compliance Engineering, Fall 1993, pp. 1–8.
"Biosignal Pattern Recognition and Interpretation Systems" E.J. Ciaccio, et al., IEEE Engineering in Medicine and Biology, Dec. 1993, pp. 106–113.

Primary Examiner—Angela D. Sykes
Assistant Examiner—Samuel Gilbert
Attorney, Agent, or Firm—Steven M. Mitchell; Mark J. Meltzer

[57] ABSTRACT

A system is provided to control operation of an implantable medical device based upon detected EMI (electromagnetic interference). A correlator produces a correlation function indicating the level of an EMI component of an input biomedical signal that includes a biomedical signal component and an EMI component, and that is monitored relative to a predetermined threshold to allow the device to operate in a normal manner as long as the intensity or level of the EMI component is such that it does not affect or interfere with device operation. One or more remedial measures may be selected in the event the level of the EMI component exceeds a predetermined threshold. The system is useful with any electronic device which receives an electronic information signal which may include an EMI component.

27 Claims, 4 Drawing Sheets

CORRELATOR BASED ELECTROMAGNETIC INTERFERENCE RESPONSIVE CONTROL SYSTEM USEFUL IN MEDICAL DEVICES

FIELD OF THE INVENTION

The present invention relates generally to EMI detection and measurement and preventing EMI from disrupting normal control system operations. More particularly, the present invention relates to controlling implantable medical devices in response to electrostatic, magnetic and/or electromagnetic interference.

BACKGROUND OF THE INVENTION

Although implantable medical devices are designed to be well shielded from electrostatic, magnetic and/or electromagnetic interference ("EMI"), it is still possible that electromagnetic signals may be picked up by the device, for example at the sensing point of the device, through rectification or other forms of detection. As used in this application, EMI is intended to include electromagnetic radiation, magnetic fields and electrostatic fields. It is therefore also a common practice to provide filters, such as bandpass filters, in implantable devices to suppress or attenuate any EMI that may have been picked up by the device. Other filters may include adaptive notch filers, spectral shaping filters, frequency-shift filters, and Kalman filters. However, such filters may not be completely effective in eliminating interference with device operation due to the presence of EMI. Additionally, an implantable device must be as small as possible. Accordingly, the space available within the device for filters is limited, and the complexity of the filter used in designing the device is therefore also limited.

Such EMI, if not successfully suppressed, can have serious consequences in implantable, electronically controlled medical devices. For example, in implantable cardiac devices, such as defibrillators, EMI (especially pulsed RF signals) can produce a false indication of an arrhythmia, thus prompting the device to administer unnecessary and painful therapy; or EMI can mask an arrhythmia, thus preventing the device from providing possibly lifesaving therapy. There have been recent press reports of particular susceptibility of cardiac devices to pulsed digital signals of the type associated with digital cellular phones. "Stray Signals: Clutter of Airwaves Can Block Workings Of Medical Electronics", *The Wall Street Journal*, Jun. 15, 1994; and "Electromagnetic Compatibility Working Group Will Develop 'Action Plan' For Incorporating EMC Requirements Into FDA Premarket Review Process", *M-D-D-I Reports*, Sep. 19, 1994, published by F-D-C Reports, Inc.

Exposure to EMI is unavoidable in the modem world of microwave ovens, cellular telephones, radar, and high speed computers. Additionally, EMI may also result from such naturally occurring phenomena as lightning and static electricity. The problem of EMI in implantable medical devices has been addressed in the prior art by monitoring an input signal provided to the device to detect anomalous conditions that indicate the possible presence or influence of EMI.

A typical prior art implantable cardiac device receives an input signal from a sensor placed within or near a patient's heart. The input signal includes a desired biomedical signal component and, when a patient is in the presence of a strong electrostatic, magnetic or electromagnetic field, an EMI component. The EMI component may be picked up at the sensor, or it may otherwise be introduced into the signal path of the device. A detector searches for the presence of an EMI signal and allows the device to provide required therapy based on the the biomedical signal as long as an EMI signal is not detected. If an EMI signal is detected above a certain level, the assumption is made that it is interfering with operation of the device and operation of the device is inhibited until such time as the EMI signal is reduced to a tolerable level.

For example, J. Kenny, *Demand Cardiac Pacer With Fast Rate For Indicating Interference*, U.S. Pat. No. 3,688,776 (5 Sep. 1972) describes a cardiac pacing device that detects EMI in a feedback path, based upon signal level or rate, and in response inhibits normal device operation. The device alerts a user to the presence of EMI by operating at a user noticeable high pace frequency. See, also R. Brownlee, G. Tyers, *Cardiac Pacing Apparatus With Electromagnetic Interference Protection*, U.S. Pat. No. 4,091,818 (30 May 1978) which describes a cardiac pacing device that includes a first channel for a demand pacing electrode and a second channel adapted to sense EMI. Upon EMI detection, the device produces a control signal that overrides demand pacing and reduces pacing to a fixed safe operating rate until such time as the interference is no longer detected.

Other art that discloses the detection of EMI in implantable medical devices includes I. Ibrahim, *Implantable Medical Devices Employing Capacitive Control Of High Voltage Switches*, U.S. Pat. No. 5,178,140 (12 Jan. 1993) which describes an implantable cardiac device having a common mode switch for rejecting common mode noise; and W. Irnich, *Interference Recognition Circuit in A Heart Pacemaker*, U.S. Pat. No. 4,516,579 (14 May 1985) which describes a pacing device that includes a decision circuit that recognizes a discriminator output signal as either an interference signal, which is not passed to a timing circuit, or as a heart action signal, which is passed to the timing circuit.

In *Cardiac Sense Amplifier With Pattern Recognition Capabilities*, U.S. Pat. No. 4,913,146 (3 Apr. 1990) to DeCote, Jr., a system is described in which a microprocessor is used with a noise detection and cancellation system to provide a digitized cardiac signal which is asserted to be free of noise. Such a system would be difficult to effectively implement.

Accordingly, typical approaches to solving the problem of EMI interference with the operation of implantable medical devices immediately interrupt normal device operation when EMI is detected. However, I have discovered a technique for detecting the presence of EMI in such devices that allows the device to operate in a normal manner in the presence of tolerable levels of EMI, or that can be used to discriminate between different levels or intensities or types of EMI to determine whether such EMI is actually a threat to normal device operation. Instead of merely indicating the detection of EMI, the invention can be used to determine whether or not the EMI is actually influencing the normal operation of a device and if so, to what degree.

SUMMARY OF THE INVENTION

In accordance with the present invention, an implantable medical device is provided which includes a correlator for receiving (a) a biomedical signal that may include an EMI component and (b) an EMI signal. The correlator produces a correlation function that is indicative of the EMI component present in both signals, whereby operation of the medical device is controllable in response to the correlation function.

Thus the invention provides a method and apparatus for detecting the presence and/or influence of EMI in implantable medical devices, such as devices that are used for cardiac pacing and defibrillation, through correlation of an EMI signal with the internal biomedical signal that the device is supposed to monitor. In the illustrative embodiment, a positive correlation indicates that EMI is invading the device and may interfere with its operation. When the intensity of the EMI or the relative degree or level of EMI influence or invasion passes a predetermined threshold, such that it is affecting the accurate sensing of the desired biomedical signal, one or more remedial actions are enabled. The invention therefore allows the implanted device to function in a normal way in the presence of EMI, but monitors the intensity of the EMI in the biomedical signal, such that one or more remedial measures may be applied when the EMI level or influence exceeds a predetermined, safe threshold.

The implantable device made in accordance with the illustrative embodiment of the invention includes a receiver or detector that is adapted to detect local EMI. A detected EMI signal and a device input signal, for example a patient electrocardiogram signal, are both coupled to the correlator. A positive correlation between the two signals indicates that an EMI component of the input signal is influencing the sensing function and/or operation of the device. The EMI component may trigger various staged alerts or remedial measures, depending upon the intensity of the EMI. These corrective measures may include, for example, any or all of the following:

1. The ability of the device to issue various commands or therapies may be inhibited until the level of the detected EMI has decreased.

2. A patient alarm may be actuated when the level of the detected EMI exceeds a predetermined threshold, thereby alerting the patient that he is in the vicinity of a dangerous source of EMI.

3. A spectrum analyzer may be operated to analyze and/or store a time or location indexed representation of the EMI component of the input signal to allow a determination to be made of which patient activities or locations exposed the patient to potentially dangerous levels of EMI. The stored EMI component might also aid in identifying the source of the EMI.

4. Depending upon the nature and level of the interference, for example when pulsed interference is detected, the biomedical signal may be blanked and a replacement signal, derived from either a previous normal input signal, a stored signal, or synthesized signal, may be substituted therefor.

5. An out of phase EMI cancellation signal may be provided.

While the invention finds immediate use in the field of implantable medical devices, it also has utility in diverse applications such as aircraft or vehicular control systems. There has been considerable concern about possible interference with navigational and flight control systems in aircraft caused by EMI arising from operation of passenger devices such as computers and cellular phones. There have been suspected EMI caused crashes of military fly-by-wire aircraft in the close vicinity of ground-based high powered broadcast and communication transmitters. The invention is easily adapted to aircraft by simply using an in-cabin and/or external antenna to receive EMI and use this to correlate with an input from a flight control signal to see if EMI is influencing the signal. If an objectionable level of correlation is found, alarms may be sounded or corrective measures such as reversion to manual controls may be instituted. Thus the invention can be used to determine the presence of an EMI component in any information signal.

The invention can also be used to make a test apparatus to investigate and document the susceptibility of any electronic apparatus, device or system to EMI.

DETAILED DESCRIPTION OF THE INVENTION

The invention provides a method and apparatus for detecting dangerous and/or potentially dangerous intensities of EMI that could interfere with or affect the operation of an implantable medical device, such as a cardiac pacemaker or defibrillator. The method and apparatus of the invention allow normal implanted device operation, even in the presence of certain levels of EMI. A variety of staged remedial measures are applied in the event the actual interference caused by the EMI is such that implanted device operation cannot or should not be maintained.

Figure 1:
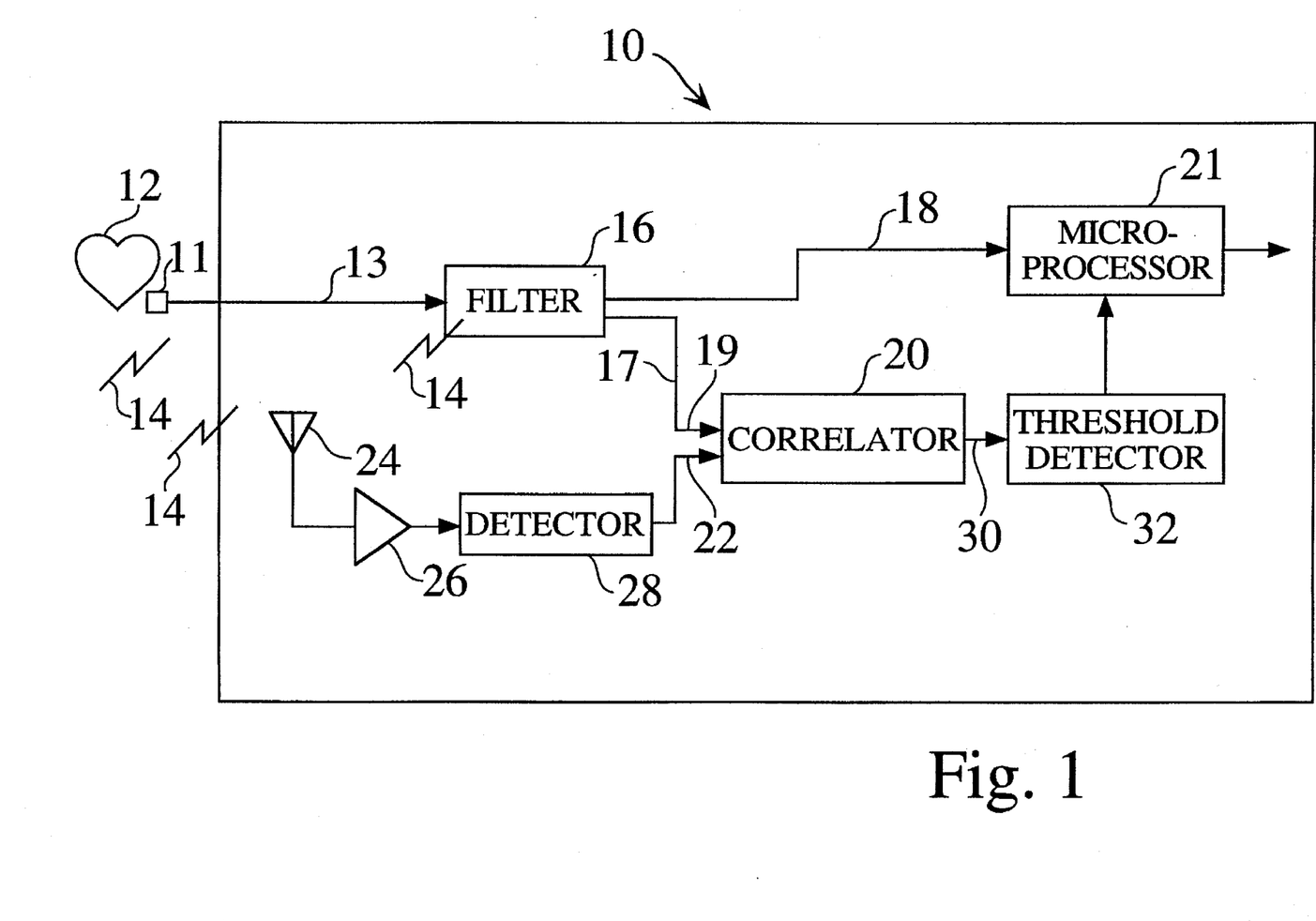
FIG. 1 is a block schematic diagram showing an apparatus for detecting EMI in an implantable medical device according to an embodiment of the invention.

FIG. 1 is a block schematic diagram that shows an apparatus for detecting EMI in an implanted cardiac device 10 according to one embodiment of the invention. In FIG. 1, a sensor 11 that is placed in or near a patient's heart 12 produces a biomedical signal that may include such information as patient ECG. The biomedical signal is provided on line 13, which may, for example, be a sensing lead, to the input of the cardiac device. If the patient is exposed to EMI 14, the input signal may also include an EMI component.

The biomedical signal, including the EMI component, is coupled to a filter 16 to remove as much of the EMI component and/or noise from the biomedical signal as possible. The filter may be any known filter that is adapted to reject a broad spectrum of EMI, for example a band pass filter, while passing the desired biomedical signal to the internal circuitry of the implanted device without undue attenuation of the biomedical signal. For an example of a filter that may be used in an implantable cardiac device, see K. Carroll, B. Pless, *Implantable Cardiac Defibrillator Employing An Improved Sensing System with Non-Binary Gain Changes*, U.S. Pat. No. 4,972,835 (27 Nov. 1990), which patent is incorporated herein by reference.

After filtering, the biomedical signal is coupled via line 17 to a first input channel 19 of a correlator 20. Although correlators have been used in noise processing for many years, see J. Bendat, *Principles and Applications Of Random Noise Theory*, (J. Wiley, 1958) pp. 302–05, the present invention incorporates a correlator in a manner that is novel and useful in the detection of EMI in implantable medical devices. For a general overview of correlators, see R. H. Roberts, *Technical Tricks, All About Correlators*, (Spread Spectrum Scene, Feb. 1993) pp. 10–11. It should also be recognized that the term correlator, as used herein, is not limited to specific hardware items called correlators (such as correlator chips), but also applies to the equivalent function performed by software or a combination of hardware and software.

The filtered input biomedical signal is also coupled via line 18 to other circuitry including microprocessor 21 within the device 10 for use during normal operation of the device. For example, if the device is a cardiac pacer, the input signal can provide the device with an indication of patient ECG, and thereby enable the device to establish a proper pacing rate via conventional pacing circuitry including microprocessor 21.

A second channel 22 of the correlator 20 is adapted to receive an EMI signal. The EMI signal is produced when EMI 14 is received or detected at a point of reception, such as provided by an antenna 24 that may be situated near but separate from the sensor 11, and/or at or within the device 10 itself. It should be noted that for optimal operation the antenna 24 should be physically separated from the sensor 11 so that it does not receive a significant level of the heart signal. Any part of the information signal such as the ECG which is received by the antenna 24 will be identified as EMI, thus to some degree defeating the purpose of the invention.

The EMI need not be received with an antenna, but may be received with any appropriate pickup device or devices. For example, multiple pick-up devices that are responsive to a selected frequency or bandwidth may be provided to cover a wide spectrum of potential sources of EMI; inductive pick-up devices may be provided to detect magnetic interference that may disrupt operation of the medical device; various RF pick-up devices may be provided to detect EMI; and microwave sensitive pick-up devices may be provided to detect pulsed interference of the type often associated with radar transmitters. Optoelectronics of Fort Lauderdale, Fla., currently markets a pocket sized near field receiver (both AM and FM types are available) called the INTERCEPTOR. These receivers automatically capture, demodulate and indicate the field strength of strong RF signals from approximately 30 MHz through 2 GHz without manual tuning. This type of technology might be useful as an EMI receiver in the instant invention. Additionally, one or more locations may be monitored in the signal processing path of the medical device to locate any possible point of EMI signal entry to the medical device, and thereby identify EMI along the entire signal path of the medical device.

The EMI signal is amplified by an amplifier 26, and the amplified EMI signal is coupled to a detector 28. Detection may include any of various techniques, such as AM or FM demodulation, rectification, and analog-to-digital conversion. Demodulation is not strictly necessary, but may be useful. In the case of RF interference and especially in the case of CW (continuous wave) or pulsed CW, merely sensing the presence or absence of an interfering signal may provide sufficient information to conduct successful correlation. The detected EMI signal is coupled to the second channel 22 of the correlator 20. Alternatively, the EMI signal need not be detected, but rather may be coupled directly to the second channel 22 of the correlator. The EMI signal may also be coupled to the correlator through filter 16 or a comparable filter, instead of being coupled directly to the correlator after detection, to shape the EMI signal in much the same way as the biomedical signal is shaped by the filter, such that the EMI signal has similar characteristics to those of the biomedical signal.

The two signals coupled to the two input channels 19 and 22 of the correlator 20 each include an EMI component. However, the signal channel from the patient's heart 12 comprises a biomedical signal containing both cardiac information and an EMI component. The correlator uses the EMI signal and the biomedical signal to produce a correlation function on correlator output line 30, representative of the EMI component of the biomedical signal. The correlation function indicates the relative level of the EMI component of the biomedical signal. It should be noted that where a software correlator is used, two separate input ports are not necessarily needed since the two signals could be multiplexed on a single input line. Also, the correlation does not necessarily have to be performed in real time. Depending on the application, the biomedical signal and EMI signals may be temporarily stored in memory with the correlation performed in near real time. With an implantable defibrillator, the system will be effective as long as the device responds to the presence of the EMI within a few hundred milliseconds or even a few seconds since there is always some delay between the detection of an ECG signal and the diagnosis of an arrhythmia and delivery of a therapy.

In the preferred embodiment of the invention, correlator 20 is used to identify a common periodic component in two signals (i.e. the biomedical signal and the EMI signal), for example by integrating a product of the two signals over time. More modern correlation techniques involve digitizing the signals and processing them using serial sliding or parallel type correlators such as those described in the aforementioned article "All About Correlators". The resulting correlation function identifies the common periodic or time related component in the two signals. In the invention, this common component is the EMI component of the biomedical signal. If there is a significant EMI component in the biomedical signal after the signal is filtered, a significant correlation function is produced.

The apparatus of FIG. 1 also includes a threshold detector 32 that is responsive to the correlation function produced by the correlator. Depending upon the level of the EMI component of the biomedical signal, as indicated by the correlation function, the threshold detector is operable to signal microprocessor 21 to initiate one or more remedial actions, as discussed below in connection with FIG. 2.

Figure 2:
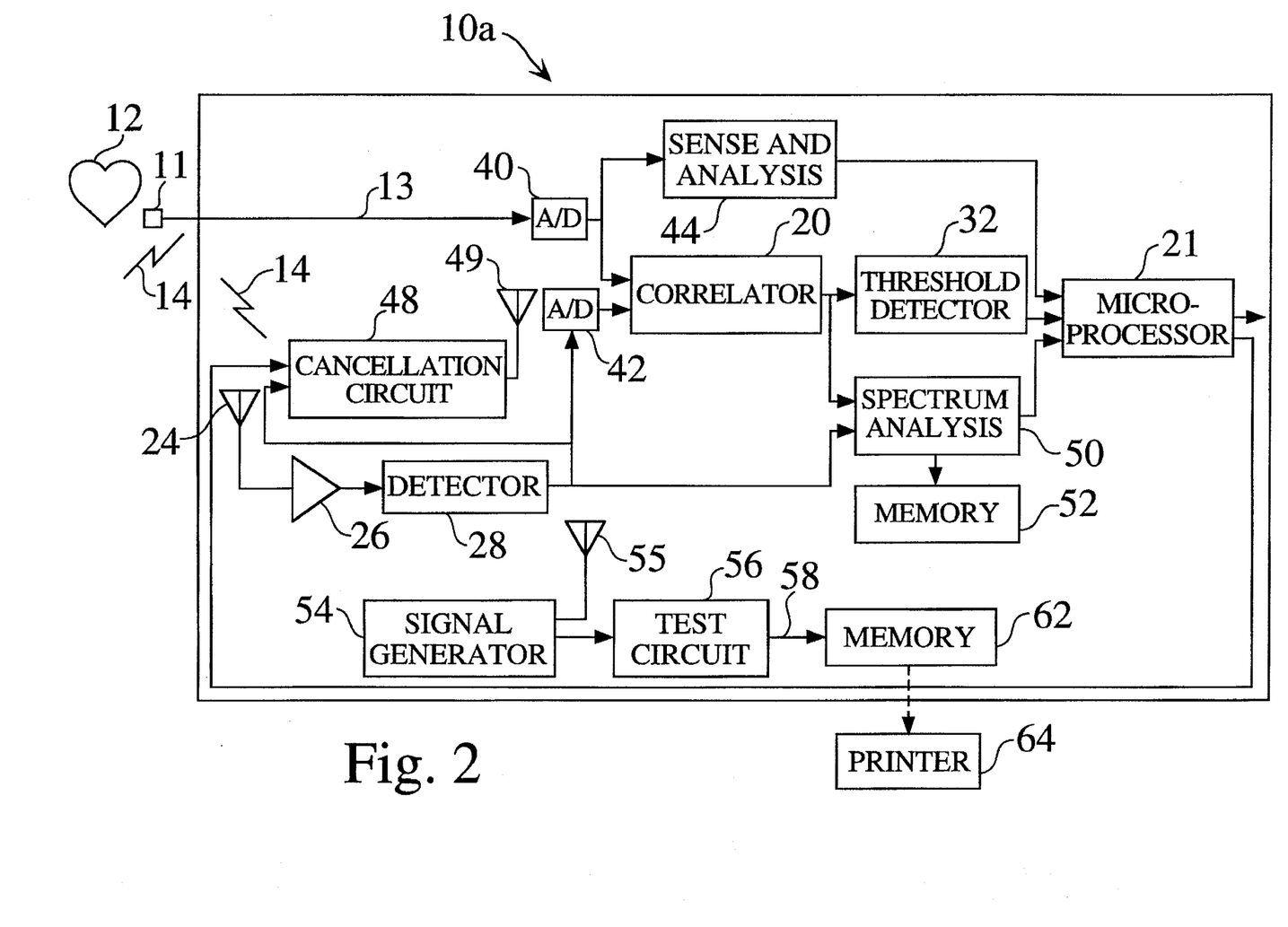
FIG. 2 is a block schematic diagram showing an apparatus for detecting EMI in an implantable medical device according to another embodiment of the invention.

FIG. 2 is a block schematic diagram in which an apparatus for detecting EMI having an intensity that would interfere with operation of an implantable medical device 10a is shown according to another embodiment of the invention. In the figure, a biomedical signal on line 13 from a sensor 11 located at or near a patient's heart 12 is coupled to an analog-to-digital converter 40. The biomedical signal from the patient's heart may also include an EMI component when EMI 14 is present. A receiver, such as antenna 24, receives an EMI signal 14 which is amplified by amplifier 26 and detected by a detector 28. The foregoing elements of the invention, with the exception of the analog-to-digital converter, function in a manner similar to those of the embodiment of the invention discussed above in connection with FIG. 1.

The EMI signal is coupled to the input of a second analog-to-digital converter 42. The outputs of both analog-to-digital converters are coupled to respective inputs of a correlator 20. The correlator is adapted to identify the EMI component of the biomedical signal by application of well known correlation techniques, such as discussed above in connection with FIG. 1.

The correlator 20 produces as an output signal a correlation function that is coupled to a threshold detector 32. When the presence of an EMI component in the biomedical signal is indicated by correlator 20, the level of the EMI component is detected by the threshold detector 32. If the level of the EMI component exceeds any of one or more predetermined thresholds, the threshold detector output to a microprocessor 21 provides a signal to microprocessor 21 to initiate any of one or more staged remedial actions, such as:

1. An emergency interrupt signal that commands the implanted device to execute a predetermined sequence of actions. Such actions may include, for example, suspension of device operation and inhibition of device therapy.

2. A patient warning signal that may be, for example a small electric shock, a change in pacing rate, or an audible signal is generated. In this way, the patient is alerted when the intensity of EMI is such that it is not safe to remain at the current location. The patient may then move to another location when the intensity of the EMI component falls to a tolerable level. When the intensity of the EMI decreases to a safe level the patient alarm is discontinued.

3. A replacement signal is provided that may be either a stored signal, a derived signal, or a synthesized signal. This can take the form of a nominal waveform (which is associated with a normal biomedical signal) being generated and connected so as to replace the EMI influenced actual biomedical signal until such time as the EMI intensity drops to an acceptable level.

4. An out of phase EMI cancellation signal is provided. For example, microprocessor 21 provides a signal to EMI cancellation circuit 48 to transmit via antenna 49 a signal that is similar to the EMI but is 180° out of phase therewith, to substantially cancel the effect of the EMI. When microprocessor 21 provides a signal to cancellation circuit 48, the cancellation circuit will be gated to receive an EMI signal from the output of detector 28 for processing, and to transmit an out of phase cancellation signal via its antenna. Alternatively, and perhaps more practically, a cancellation signal which is an electronic signal rather than RF signal may be transmitted, via hard wire structure, directly to the analog to digital converter inputs or to some other point in the circuitry where it can be added to an EMI influenced signal to cancel out the EMI component. For example, the cancellation signal could be a digital signal which is added downstream of the analog to digital converter.

The output of the detector 28 may also be coupled to a spectrum analyzer 50, which can be used in conjunction with the correlator function from the correlator 20 to determine the portion of the electromagnetic spectrum in which the EMI is occurring, and thereby identify the frequency of the EMI. The term "spectrum analyzer" is used broadly here and is not limited to the typical apparatus which plots or displays signal intensity on a y axis and frequency on an x axis. In this invention, a spectrum analyzer is any apparatus which derives useful information about an EMI signal such as its carrier frequency, modulation, pulse rate or any other parameter which would be useful in classifying and possibly identifying the source of the EMI signal. A memory 52 may be provided to store time indexed or even location indexed (at such a time as miniature GPS (Global Positioning Satellite), LORAN or other types of electronic navigation receivers become available for incorporation into implantable devices) frequency, pulse rate or other EMI information produced by the spectrum analyzer. The stored EMI information may be retrieved at a later time and linked to the patient's locations and activities at certain times to determine which of those locations and/or activities have exposed him to dangerous levels of EMI. In this way, the patient can avoid such locations and/or activities in the future and thereby lessen the likelihood of interruption to implanted device operation due to EMI. The output of spectrum analyzer 50 is coupled to microprocessor 21 to signal the microprocessor to initiate one or more remedial actions that are programmed in response to the signal from spectrum analyzer 50.

It may be desirable during design testing or possibly even during use of an implantable device to determine the effect of various forms of EMI on correlator 20 and the resulting actions taken by microprocessor 21. To this end, a signal generator 54 is provided with an antenna 55 that is capable of transmitting a signal that is received by antenna 24 and picked up by sensor 11. Signal generator 54 is operable to test the system by providing signal waveforms having various configurations and frequencies. A signal generator circuit may be incorporated in the implantable medical device 10a to be activated by a remote RF signal command or, more practically, it may take the form of a separate unit external to the implantable medical device, for positioning in a location proximate to the implantable medical device.

Signal generator 54 is coupled to a test circuit 56 that is operable to monitor various signal points throughout device 10a. Test Circuit 56 may include its own correlator or, if practical, may utilize the correlator 20 of the medical device to determine which transmitted EMI signals are causing interference to the normal operation of the device. In this manner, test circuit 56 can detect the effect that various signal waveforms have on the signal points and a readout may be provided via line 58. Readout line 58 is connected to a memory device 62 for storing data relating to the effect of various signal waveforms on the signal points. Alternatively, readout line 58 or memory device 62 could be connected to a printer 64 to provide a hard copy of the data. Signal generator 54 is programmed to generate a selected series of waveforms upon transmission of a remote command. This setup could also be useful in automatic EMI susceptibility testing of breadboarded or prototype designs for implantable device circuits or other non-medical circuits or systems where susceptibility to EMI needs to be documented.

Figure 3:
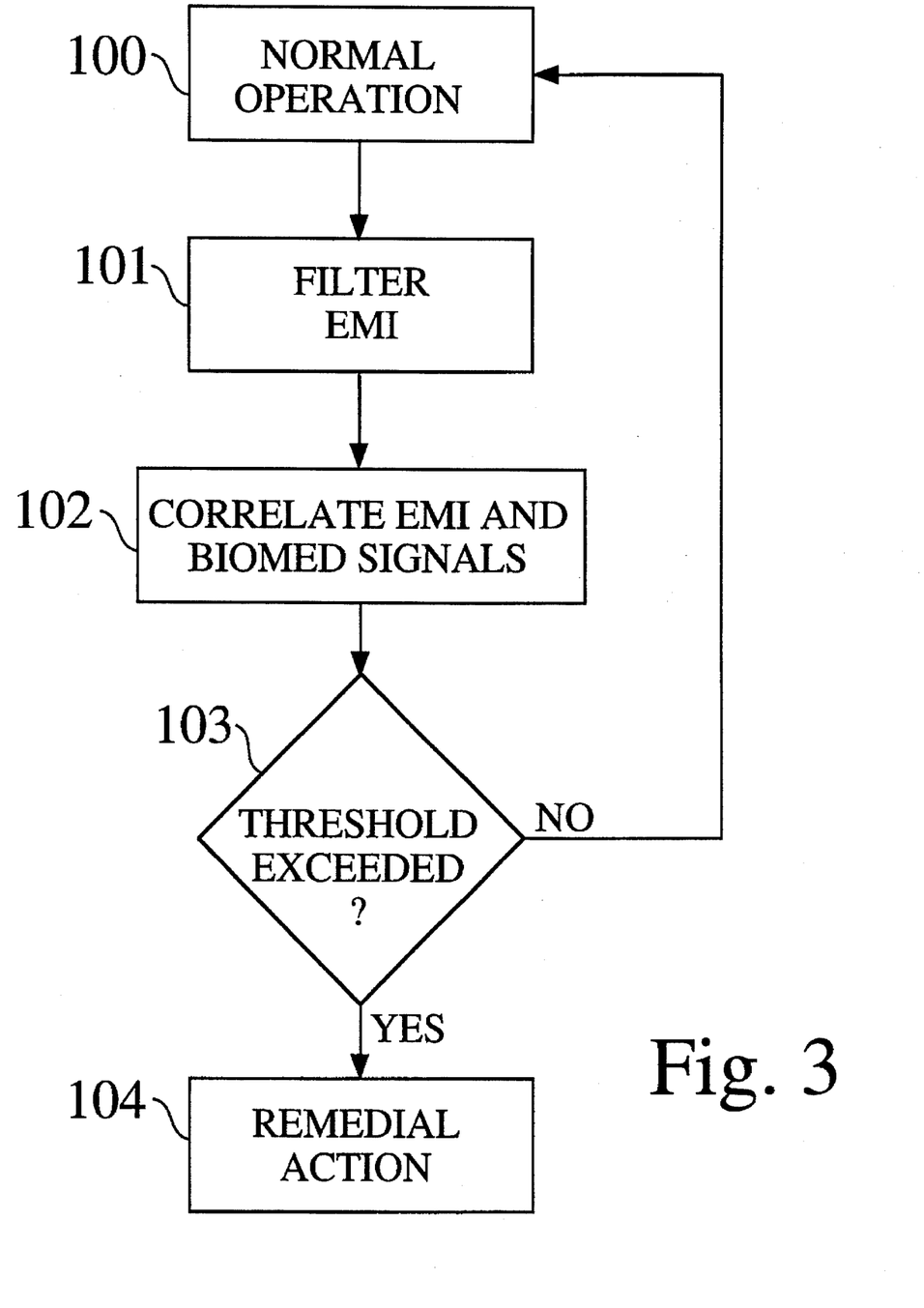
FIG. 3 is a flow diagram showing operation of an apparatus for detecting EMI in an implantable medical device according to the invention.

FIG. 3 is a flow diagram showing operation of an apparatus for detecting EMI in an implantable medical device according to the illustrative embodiment of the invention. In the figure, an implanted medical device is initially operating in a normal fashion (100). A filter is used to suppress or attenuate the EMI component of a biomedical signal that is input to the device (101). A correlator is provided with a biomedical signal and a separate EMI signal to produce a correlation function indicative of the presence of EMI (102) in the biomedical signal. Then the level of the correlation function is tested by a threshold detector (103). In the event the level of the EMI is at a sufficiently high level that it exceeds a predetermined threshold (103), then various staged actions may be taken, as discussed above. If the level of the EMI is such that the implanted device may be allowed to continue normal operation without any adverse affects, the EMI detection, and normal implanted device operation, continue.

Figure 4:
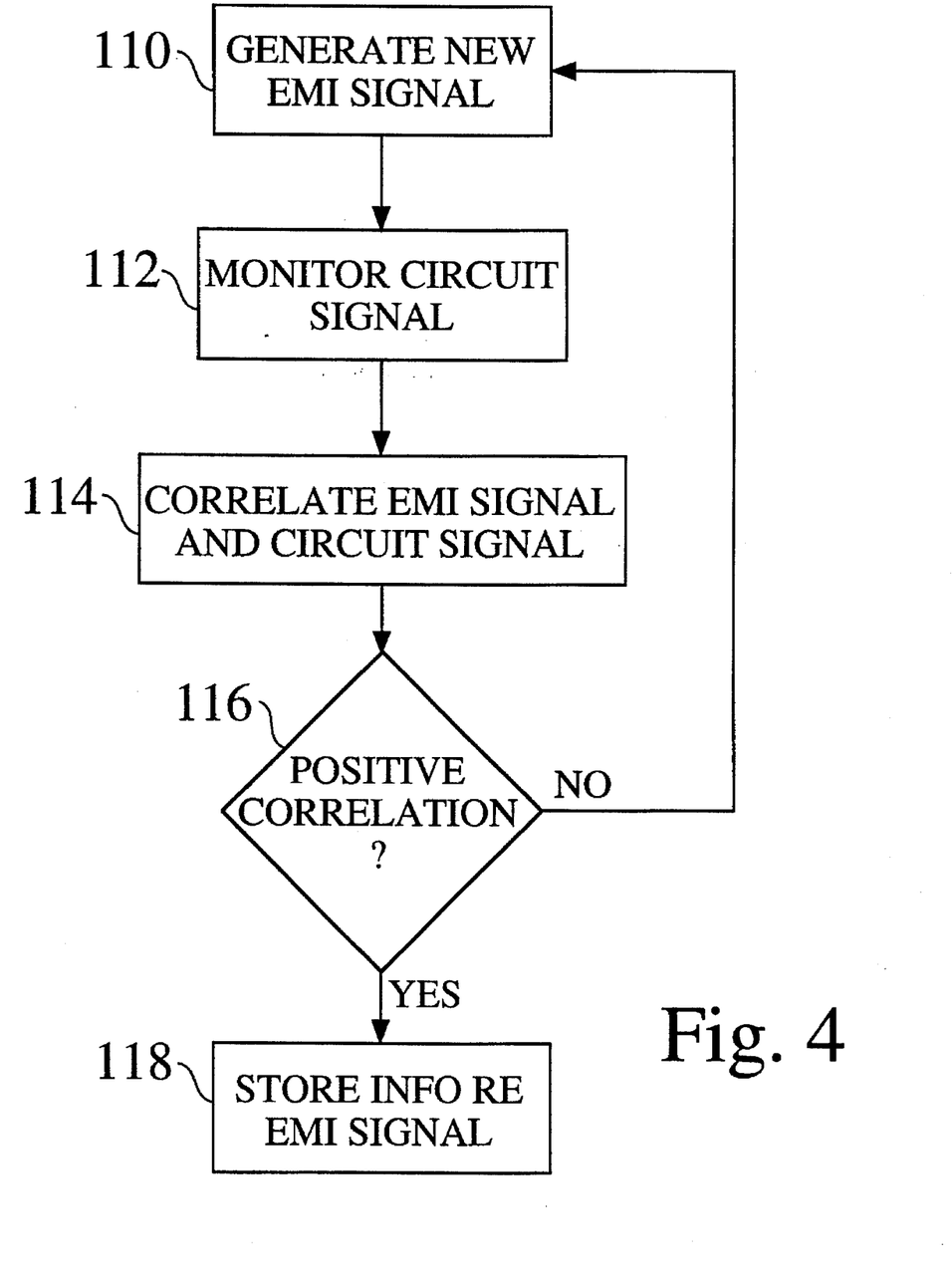
FIG. 4 is a flow diagram showing operation of an apparatus for testing the susceptibility of a circuit to EMI.

FIG. 4 is a flow diagram for testing the susceptibility of a circuit to EMI. This is accomplished by generating an EMI signal (110), using the invention to monitor a circuit signal (112) and correlating the signals (114) to determine susceptibility (116). The circuit signal, as described above, can be any information-bearing circuit parameter such as current or voltage at a particular point in the circuit. If positive correlation is found, information regarding the EMI signal is stored (118). If positive correlation is not found, a new EMI signal is generated and the test is continued.

Although the invention is described herein with reference to the preferred embodiments, one skilled in the art will readily appreciate that other applications may be substituted for those set forth herein without departing from the spirit and scope of the present invention. For example, the invention has been described in terms of cardiac application. However, the invention can be applied to other medical applications that use a receiver or pick-up device to generate a biomedical signal, such as the internal monitoring of brain activity and of internal chemical levels, such as blood sugar. Additionally, the various staged remedies may be provided alone or in combination as appropriate, and other remedies may be substituted therefor, depending upon the application for which the invention is used. Also, any of various schemes may be used to cancel the EMI component of the signal, including filters, analog an/or digital signal processing, etc. The invention can also be used with other control systems such as for an aircraft where an information signal may include an EMI component. Accordingly, the invention should only be limited by the claims included below.

What is claimed is:

1. An implantable medical device, which comprises:
    a sensor for sensing a biomedical signal that may include an EMI component;
    a detector for receiving an EMI signal and substantially excluding said biomedical signal; and
    a correlator for receiving said biomedical signal and said EMI signal, said correlator producing a correlation function that is indicative of said EMI component.

2. An implantable medical device as defined by claim 1, said correlation function being indicative of a level of said EMI component.

3. An implantable medical device as defined by claim 2, including means coupled to receive an output of said correlator for providing predetermined, staged, remedial measures in response to an increasing level of said EMI component.

4. An implantable medical device as defined by claim 2, including means coupled to receive an output of said correlator for substituting a replacement signal for said biomedical signal when the level of said EMI component exceeds a predetermined threshold.

5. An implantable medical device as defined by claim 4, wherein said replacement signal is a stored signal, a derived signal, or a synthesized signal.

6. An implantable medical device as defined by claim 2, including means responsive to said correlation function for blanking said biomedical signal when the level of said EMI component exceeds a predetermined threshold.

7. An implantable medical device as defined by claim 2, including means responsive to said correlation function for generating a patient alarm when the level of said EMI component exceeds a predetermined threshold.

8. An implantable medical device as defined by claim 2, including means for providing an out of phase EMI cancellation signal when the level of said EMI component exceeds a predetermined threshold.

9. An implantable medical device as defined by claim 1, including means for inhibiting at least some device operation when a level of said EMI component as indicated by said correlation function exceeds a predetermined threshold.

10. An implantable medical device as defined by claim 1, including circuitry for processing said biomedical signal and further including a signal generator to provide a test signal and a test circuit responsive thereto, operable to monitor a response of said circuitry for processing said biomedical signal to said test signal.

11. An implantable medical device as defined by claim 1 and further including:
    a spectrum analyzer;
    a location determining means;
    a memory; and
    means for providing in said memory location indexed spectrum analysis information when the level of said EMI component exceeds a predetermined threshold.

12. An implantable medical device as defined by claim 1 and further including:
    a spectrum analyzer;
    a time determining means;
    a memory; and
    means for providing in said memory time indexed spectrum analysis information when the level of said EMI component exceeds a predetermined threshold.

13. An implantable medical device, which comprises:
    a correlator having a first input and a second input;
    said first input adapted for receiving a biomedical signal that may include an EMI component;
    said second input adapted for receiving a EMI signal and substantially excluding said biomedical signal;
    said correlator producing a correlation function that is indicative of said EMI component, whereby operation of the medical device is controllable in response to said correlation function;
    said correlation function being indicative of a level of said EMI component;
    a threshold detector operable in response to said correlation function for providing an output signal indicative of said EMI component exceeding a predetermined threshold; and
    means for controlling operation of said medical device in response to said threshold signal.

14. An implantable medical device as defined by claim 13, including a first analog to digital converter coupled to said first input; a second analog to digital converter coupled to said second input; and an EMI detector coupled to an input of said second analog to digital converter.

15. An implantable medical device as defined by claim 14, including a spectrum analyzer coupled to an output of said EMI detector and adapted for receiving a signal corresponding to said EMI signal.

16. A medical device control method, which comprises the steps of:
    providing a correlator for receiving (a) a biomedical signal that may include an EMI component, and (b) an EMI signal;
    producing a correlation function via said correlator that is indicative of said EMI component; and
    controlling the operation of a medical device in response to said correlation function.

17. The method of claim 16, including the step of determining if the EMI component has exceeded a predetermined threshold.

18. The method of claim 17, including the step of inhibiting at least certain operations of said medical device if said EMI component exceeds said predetermined threshold.

19. The method of claim 17, including the step of generating a patient alarm if said EMI component exceeds said predetermined threshold.

20. The method of claim 17, including the step of providing a predetermined remedial measure if said EMI component exceeds said predetermined threshold.

21. The method of claim 20, wherein said remedial measure comprises one or more of the steps of (a) substituting a replacement signal for said biomedical signal, (b) generating a patient alarm, (c) inhibiting device operation, (d) providing an out of phase EMI cancellation signal.

22. The method of claim 17, including the steps of providing waveforms having various configurations; monitoring various signal points in the medical device; and detecting the effect that various waveforms have on said signal points.

23. In an electronic circuit which includes a sensor for electronically sensing at least one parameter, an EMI detection circuit comprising:

a correlator having a first input and a second input, said first input adapted for receiving a signal from said sensor that may include an EMI component and said second input adapted for receiving a EMI signal and substantially excluding a signal of said at least one parameter; and said correlator producing a correlation function that is indicative of said EMI component.

24. An EMI detection circuit as defined by claim 23, including a threshold detector coupled to receive said correlation function for providing an output signal indicative of said EMI component exceeding a predetermined threshold; and means for controlling operation of an electronic apparatus in response to said threshold signal.

25. An EMI detection circuit as defined by claim 23, including a first analog to digital converter coupled to said first input; a second analog to digital converter coupled to said second input; and an EMI detector coupled to an input of said second analog to digital converter.

26. An electronic circuit comprising:

a sensor for receiving an information signal which may include an EMI component;

a sensor for receiving an EMI signal and substantially excluding said information signal; and a correlator coupled to said sensors to receive said EMI signal and said information signal, said correlator producing a correlation function indicative of said EMI component in said information signal.

27. An electronic circuit as defined by claim 26, wherein said sensor for receiving an EMI signal comprises a sensor responsive to magnetic fields.

* * * * *